(12) United States Patent (10) Patent No.: US 11,517,200 B2
Herzlinger et al. (45) Date of Patent: *Dec. 6, 2022

(54) PROCESSING IMAGES FROM ANNULAR RECEPTOR ARRAYS

(71) Applicant: Intuitive Surgical Operations, Inc., Sunnyvale, CA (US)

(72) Inventors: Peter M. Herzlinger, Saratoga, CA (US); Giuseppe Maria Prisco, Calci Pisa (IT); Vincent Duindam, Mountain View, CA (US); David Q. Larkin, Menlo Park, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 812 days.

This patent is subject to a terminal disclaimer.

(21) Appl. No.: 16/355,366

(22) Filed: Mar. 15, 2019

(65) Prior Publication Data

US 2019/0209016 A1 Jul. 11, 2019

Related U.S. Application Data

(60) Continuation of application No. 15/783,967, filed on Oct. 13, 2017, now Pat. No. 10,264,978, which is a
(Continued)

(51) Int. Cl.
*A61B 5/00* (2006.01)
*A61B 1/267* (2006.01)
(Continued)

(52) U.S. Cl.
CPC .......... *A61B 5/0084* (2013.01); *A61B 1/0005* (2013.01); *A61B 1/00096* (2013.01);
(Continued)

(58) Field of Classification Search
CPC . A61B 5/0084; A61B 1/0005; A61B 1/00096; A61B 1/00165; A61B 1/00181;
(Continued)

(56) References Cited

U.S. PATENT DOCUMENTS 4,238,680 A * 12/1980 Anger .................. H01J 37/153
250/397
5,547,455 A * 8/1996 McKenna ............ A61B 1/0005
348/65
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Sanjay Cattungal

(57) ABSTRACT

Vision systems on catheters, cannulas, or similar devices with guiding lumens include receptors distributed in annular areas around respective lumens. Each of the receptors has a field of view covering only a portion of an object environment, and the field of view of each of the receptors overlaps with at least one of the fields of view of the other receptors. A processing system can receive image data from the receptors of the vision systems and combine the image data to construct a visual representation of the object environment.

20 Claims, 4 Drawing Sheets

Related U.S. Application Data division of application No. 13/944,999, filed on Jul. 18, 2013, now Pat. No. 9,801,551.

(60) Provisional application No. 61/673,799, filed on Jul. 20, 2012.

(51) Int. Cl.
  *A61B 1/00* (2006.01)
  *A61B 1/06* (2006.01)
  *A61B 5/08* (2006.01)

(52) U.S. Cl.
  CPC ...... *A61B 1/00165* (2013.01); *A61B 1/00181* (2013.01); *A61B 1/00183* (2013.01); *A61B 1/0607* (2013.01); *A61B 1/2676* (2013.01); *A61B 1/00009* (2013.01); *A61B 1/00167* (2013.01); *A61B 1/00193* (2013.01); *A61B 1/0676* (2013.01); *A61B 1/0684* (2013.01); *A61B 5/08* (2013.01); *A61B 5/6852* (2013.01); *A61B 2576/00* (2013.01)

(58) Field of Classification Search
  CPC . A61B 1/00183; A61B 1/0607; A61B 1/2676; A61B 1/00009; A61B 1/00167; A61B 1/00193; A61B 1/0676; A61B 1/0684; A61B 5/08; A61B 5/6852; A61B 2576/00
  See application file for complete search history.

(56) References Cited

U.S. PATENT DOCUMENTS

| | | | | |
|---|---|---|---|---|
| 5,606,170 A | * | 2/1997 | Saaski | G01N 21/6428 250/227.14 |
| 6,118,516 A | * | 9/2000 | Irie | G03F 9/7015 355/53 |
| 6,652,452 B1 | * | 11/2003 | Seifert | A61B 1/00096 600/140 |
| 7,942,814 B2 | * | 5/2011 | Remijan | A61B 1/018 600/121 |
| 8,840,566 B2 | * | 9/2014 | Seibel | A61B 10/0266 600/566 |
| 9,801,551 B2 | | 10/2017 | Herzlinger et al. | |
| 10,264,978 B2 | | 4/2019 | Herzlinger et al. | |
| 2002/0099267 A1 | * | 7/2002 | Wendlandt | A61B 1/00183 600/173 |
| 2005/0047728 A1 | * | 3/2005 | Tobiason | G01D 5/34723 385/89 |
| 2008/0137363 A1 | * | 6/2008 | Harris | A61B 5/0068 362/574 |
| 2009/0135280 A1 | * | 5/2009 | Johnston | A61B 1/0005 348/262 |
| 2009/0137893 A1 | * | 5/2009 | Seibel | A61B 1/07 600/407 |
| 2009/0147257 A1 | * | 6/2009 | Splinter | A61B 5/6852 356/364 |
| 2010/0274082 A1 | * | 10/2010 | Iguchi | A61B 1/0005 600/109 |
| 2010/0274090 A1 | * | 10/2010 | Ozaki | A61B 1/00096 600/173 |
| 2010/0317923 A1 | * | 12/2010 | Endo | A61B 1/0008 600/178 |
| 2011/0098572 A1 | * | 4/2011 | Chen | A61B 5/0066 600/463 |
| 2012/0190990 A1 | * | 7/2012 | Ohzawa | A61B 1/043 600/478 |
| 2013/0184524 A1 | * | 7/2013 | Shimada | A61B 1/07 600/109 |
| 2014/0031800 A1 | * | 1/2014 | Ben Oren | A61B 18/22 606/7 |

* cited by examiner

PROCESSING IMAGES FROM ANNULAR RECEPTOR ARRAYS

CROSS-REFERENCE TO RELATED APPLICATIONS

This patent document is a continuation and claims benefit of the earlier filing date of U.S. patent application Ser. No. 15/783,967, filed Oct. 13, 2017, which is a divisional and claims benefit of the earlier filing date of U.S. patent application Ser. No. 13/944,999, filed Jul. 18, 2013, now U.S. Pat. No. 9,801,551, which claims the priority of U.S. Provisional Pat. App. No. 61/673,799, filed Jul. 20, 2012, all of which are hereby incorporated by reference in their entirety.

BACKGROUND

Instruments used in minimally invasive medical procedures often need to provide complex operational capabilities within a limited instrument diameter. For example, a catheter used for a lung biopsy may be navigated along airways or bronchial tubes to a worksite in a patient's lung and then used as a guide for insertion and removal of other instruments such as a biopsy needle. However, a lung catheter will generally require more functionality than a simple guide tube in order to be usable. For example, to navigate airways, the lung catheter may need to be steerable, e.g., contain a mechanical system that allows remote control of the shape of the catheter and may need to include a system for determining the location of the catheter relative to natural lumens being navigated. Sensor systems using electromagnetic sensors or fiber shape sensors can be employed in the walls of a lung catheter to measure the location and pose of the catheter, which may be particularly useful for robotic or computer assisted operation of the catheter. A vision system that shows the interior of the airways, e.g., at the distal tip of the catheter, could also be useful during and after airway navigation. However, a vision system that provides a desired field of view can be challenging to accommodate within a catheter, particularly because the lumen of the catheter that guides instruments may occupy most of the center of the catheter and because the distal end of a lung catheter may be about 3 mm in diameter and have walls less than 1 mm.

SUMMARY

In accordance with an aspect of the invention, a vision system for a medical instrument can include multiple receptors located around the perimeter of the distal end of the medical instrument. The vision system can thus surround an unobstructed portion of the distal tip. The unobstructed portion of the distal tip may, for example, be the distal end of a tool channel lumen that may extend through a medical device such as a catheter, bronchoscope, endoscope, or cannula. The receptors may have limited fields of view, and an image processing system can stitch together image data from multiple receptors to construct a visual representation of an object environment of the vision system.

One specific embodiment of the invention is a system including receptors distributed in an annular area. Each of the receptors may have a field of view covering only a portion of an object environment, and the field of view of each of the receptors may overlap with at least one of the fields of view of the other receptors. An image processing system can be coupled to receive image data from the receptors and operate to combine image data from the receptors to construct a visual representation of the object environment.

Another embodiment of the invention is a medical instrument including an elongated structure such as a tube and multiple receptors distributed in an annular area at a distal tip of the elongated structure. Each of the receptors has a field of view covering only a portion of an object environment of the medical instrument, and the field of view of each of the receptors overlaps with at least one of the fields of view of the other receptors.

Yet another embodiment of the invention is a vision system including an annular substrate, and multiple image sensor chips mounted on the annular substrate.

BRIEF DESCRIPTION OF THE DRAWINGS

Use of the same reference symbols in different figures indicates similar or identical items.

DETAILED DESCRIPTION

A vision system for an elongated or tube-shaped medical instrument such as a catheter or cannula can employ multiple image receptors arranged in an annular area at a distal end of the instrument. The image receptors can collect image information from respective portions of the environment in the front of an instrument, and the image information from some or all of the image receptors can be combined to create a visual representation of the environment. For example, a medical system including a catheter in a natural lumen such as a bronchial tube may stitch together the images from multiple image receptors to form a 2D visual representation, e.g., an image, or a 3D visual representation, e.g., a stereoscopic view, of the interior of the lumen. The availability of image information from multiple viewpoints may permit further image processing. For example, the vision system for an instrument may be able to identify image features corresponding to the instrument and switch between producing a visual representation that shows the instrument in relationship to the environment at the distal end of the vision system and producing a visual representation from which the instrument has been removed, made semitransparent, or outlined for better viewing of the environment.

Figure 1A:
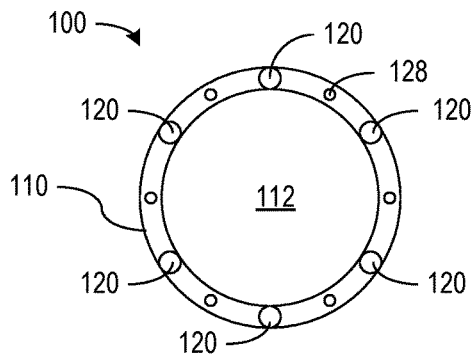
FIG. 1A shows an end view of a medical instrument containing a vision system with multiple distal receptors arranged in an annular area.

FIG. 1A shows a distal end of a medical instrument 100 employing a vision system with multiple distal receptors 120. The vision system may generally be used to provide to human observers or to automated control systems information regarding an object environment of instrument 100. The vision system may particularly produce data representing video or images of the object environment, stereoscopic views of the object environment, or 3D models mathematically representing the locations of features of the object environment. In general, the use of the term "vision" is not intended to limit the output of the vision system to an image that might be seen by a human observer or to limit the system to use of visible light. More generally, receptors 120 may provide measurements of the object environment using infrared, visible, or ultraviolet light or other wavelengths of electromagnetic radiation.

Receptors 120 in instrument 100 are positioned in an annular area at the distal end of a tube 110 or a similar elongated structure having a distal tip with an annular area available for the vision system. The annular area of FIG. 1A happens to be circular and have an opening 112 at the center of the annular area. More generally, the annular area is not required to have circular inner and outer perimeters. More generally, the annular area or opening 112 can be oval, square, or any similar shape, and opening 112, if present, may be offset from the center of the annular area. Distal receptors 120 in FIG. 1A are particularly positioned in the annular area around an opening 112 at the distal end of a tool channel lumen of medical instrument 100 so that opening 112 is unobstructed. As described further below, each distal receptor 120 may include a coherent bundle of optical fibers, one or more optical elements such as lenses that focus an image on one or more optical fibers, or an electronic imaging system such as small electronic image sensor chip. One or more illumination fiber 128 can also be set in tube 110 among distal receptors 120 or in a separate annular region to provide light for the vision system, and/or illumination fibers could be interleaved with optical fibers that receptors 120 use to conduct light between the distal and proximal ends of instrument 100. Distal receptors 120 may be but are not required to be equally spaced around the annular area of the distal end of tube 110 as shown in FIG. 1A.

Figure 1B:
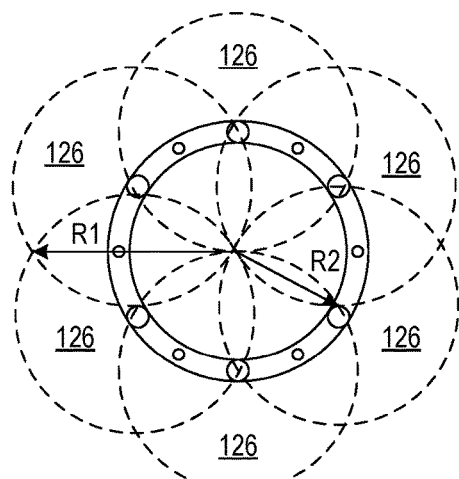
FIG. 1B illustrates the areas within the fields of view at a viewing distance from the medical instrument of FIG. 1A.

FIG. 1B shows boundaries of fields of view 126 of distal receptors 120 at some distance X0 from distal receptors 120 when digital receptors 120 are equally-spaced around the distal end of tube 110. In FIG. 1B, each field of view 126 only covers a portion of the desired object environment of the vision system. At the specific distance X0 illustrated, fields of view 126 partially overlap each other, and a point along the central axis of medical instrument 100 is at the edge of each of the fields of view 126. At closer distances, the collection of fields of view 126 does not cover a central area in front of medical instrument 100. Accordingly, if full coverage of the central area is desired, receptors 120 should be focused to provide viewing at a distance X greater than or equal to distance X0 if a view including the central axis is needed.

The combined area of the fields of view 126 at the illustrated distance of FIG. 1B provides a collective field of view that completely covers a circular area out to some radius R1 and partially covers areas at radial distances greater than radius R1. In particular, each location at distance X0 and in an area out to a transverse distance R1 from the center axis of medical instrument 100 is (unless occluded by an intervening object) within field of view 126 of at least one distal receptors 120. Image data from distal receptors 120 can thus be used to provide a 2D visual representation of an object environment out to distance R1 at distance X0. Similarly, each location at distance X0 in an area an out to a transverse distance R2 from the center axis of medical instrument 100 is (unless occluded by an intervening object) within fields of view 126 of at least two distal receptors 120, so that a 3D visual representation of an object environment out to distance R2 at distance X0 may be generated from image data that receptors 120 provide. Using a viewing distance X greater than X0 will generally provide more overlap of fields of view 126, which may be desirable for image processing as described further below. The radii R1 and R2 will depend on the focal length and numerical aperture of each receptor 120 and on the number of receptors 120. For a particular medical instrument, the desired image radius R1 or R2 and the desired viewing distance X may depend on the desired object environment to be viewed, e.g., on the size of the natural lumens such as the bronchial tubes that medical instrument 100 is intended to navigate.

Different vision systems may have different field of view requirements. A vision system used solely to navigate a natural lumen such as a bronchial tube may not need to cover the entire bronchial tube. The vision system may only need to be sufficient for determinations of the branching directions. Accordingly, a vision system may not need to cover the entire tube wall or the object area along the central axis of the instrument. Also, a full field of view and clear imaging may be desired for human visual inspection of a bronchial tube or precision targeting of tissue but may not be necessary for some other uses. It may be sufficient for receptors 120 to provide, for example, a number of fields of view that are directed at different or disjoint portions of the object environment, so that gaps are left between the portions of the object environment that are in the fields of view of receptors 120. An image processing system could use tight mechanical tolerances on the placement of receptors 120 or some global calibration of the object environment to determine where receptors 120 and associated image data are located with respect to the others receptors 120 or portions of a composite image. A visual representation generated using such image data from receptors that leave gaps in the coverage of the object environment may preserve spatial relationships by adding filler or interpolated values for pixels corresponding to "unseen" areas that are between actual images of portions of a representation of the object environment.

The embodiment of medical instrument 100 shown in FIGS. 1A and 1B employs six receptors 120, but more generally, a vision system might employ two, three, or more distal receptors to cover a desired object environment. The number of distal receptors 120 used in a particular implementation may depend on the object environment to be viewed and the resolution of each distal receptor 120. For a small device such as a lung catheter, each distal receptor 120 may need to be small enough to fit within an annular area about 0.5 mm wide, which may limit the resolution of each receptor 120. For example, the focusing element of optical portion of each distal receptor 120 may be almost ten times the active area, e.g., the end area of the optical fibers, of the distal receptor 120, so that active area can only accommodate a limited number of pixels, e.g., a limited number of optical fibers. Each receptor 120 may thus provide a pixel array that is less than 100 pixels wide, and a greater number of distal receptors 120 with narrow fields of view may be used for clear viewing of the entirety of the object environment. A vision system used for finding the bifurcations in bronchial tubes may not need a high resolution image for identification of the tunnel directions.

Figure 1C:
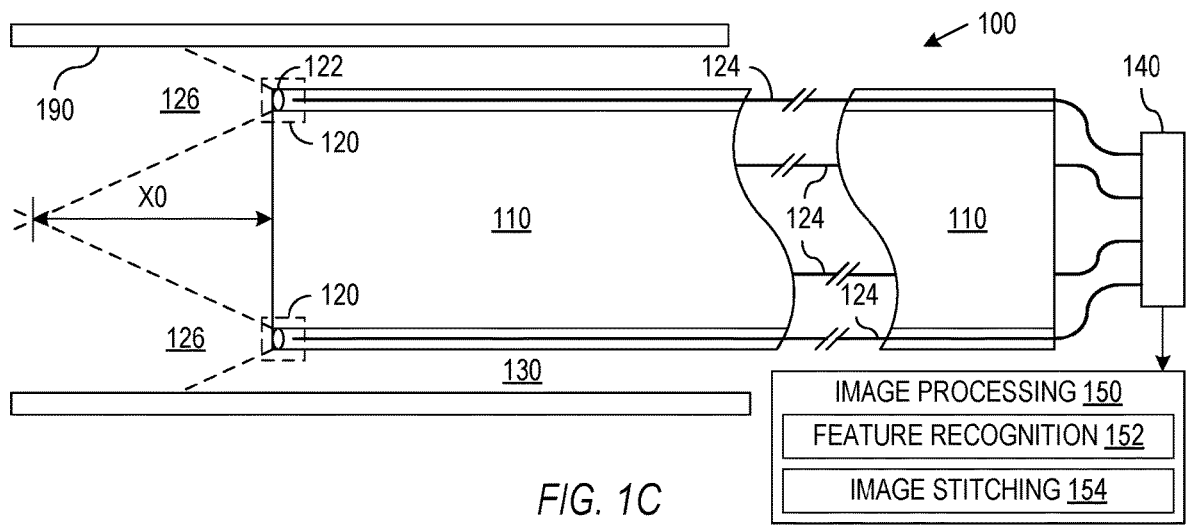
FIG. 1C shows a cross-sectional view illustrating relationships of the fields of view of the catheter of FIG. 1A when deployed in a lumen.

FIG. 1C shows a cross-sectional side view of one configuration of medical instrument 100 when used in a natural lumen 190. In the configuration illustrated in FIG. 1C, each distal receptor 120 includes a focusing element 122 positioned at the distal end of a coherent optical fiber bundle 124. Each focusing element 122 may, for example, be a gradient-index (GRIN) lens, an etched lens, or other refractive lens or a diffractive element. Each focusing element 122 may reduce the numerical aperture of the corresponding fiber bundle 124. For one specific embodiment in which medical instrument 100 is a lung catheter having a distal tip with a diameter of about 3 mm, each focusing element 122 may be selected to provide a good focus at a spot about 3 to 4 mm from the distal end of the associated coherent fiber bundle 124. Another configuration of the vision system may also employ individual optical fibers that are managed in a coherent or ordered assembly, and each optical fiber may have its own lens, e.g., a ball lens, at its distal end to provide a focus plane 3 to 4 mm away from the distal end of the fiber or lens. The resulting vision system may be similar to a fly's eye configuration but with the bundles arranged in an annular area.

Focusing elements 122 in FIG. 1C are arranged in an annular area at or near the distal end of tube 110. Each focusing element 122 of a distal receptor 120 has a field of view 126 that may depend on the size and shape of focusing element 122, the focal length of focusing element 122, a distance between focusing element 122 and the distal end of fiber bundle 124 on which focusing element 122 projects an image, and the size of fiber bundle 124. Each coherent fiber bundles 124 extends through the wall of tube 110 and may be butted up against an electronic image sensor 140. Image sensor 140 may have pixels that are smaller than each fiber, e.g., about a third of the width of each fiber in bundle 124. Coherent bundles 124 may also be imaged to respective areas of image sensor 140 with objective lenses (not shown) between the proximal ends of fiber bundles 124 and image sensor 140.

An image processing system 150 receives image data from image sensor 140 and manipulates the image data, e.g., to electronically or digitally split up and recombine the image data to create a visual representation. For example, image processing system 150 may construct an image having the shape of the combined fields of view 126 of FIG. 1B or crop such an image to show a circular or rectangular image on the computer screen. Image processing system 150 may be implemented using specialized hardware or a general purpose computer system executing suitable image processing software. Many image processing techniques are currently known and could be employed for creating a visual representation from the image data that image sensor 140 provides. Image processing system 150 may, for example, include a feature recognition module 152 and an image stitching module 154. Feature recognition module 152 may be used to identify image data corresponding to portions of medical instrument 100 or a probe that may be inserted through tube 110. Image stitching module 154 can combine image data collected by receptors 120 to form a 2D or 3D visual representation and may operate to either include or exclude from the visual representation image data corresponding to features recognized by module 152. Accordingly, image processing system 150 may construct a visual representation of the object environment with or without showing portions of a probe or medical instrument 100.

Figure 2:
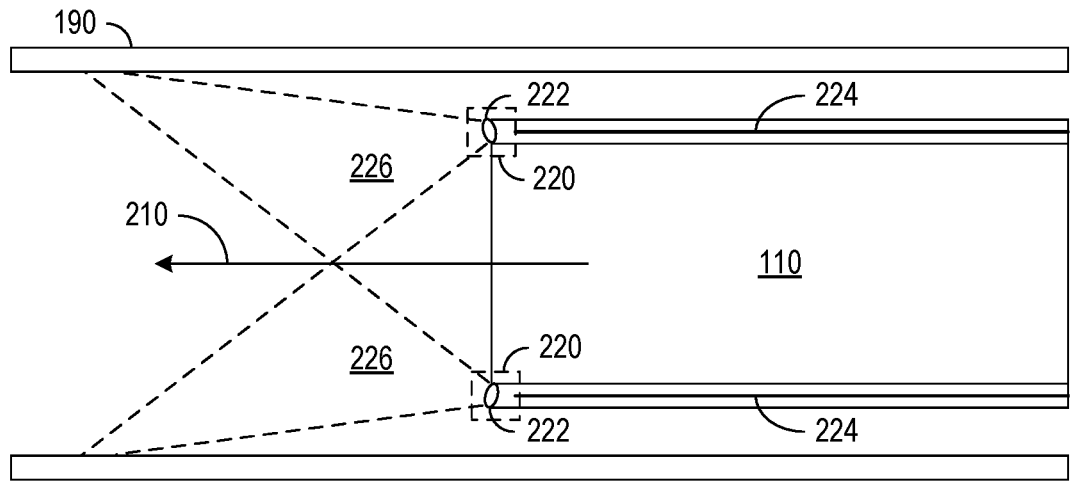
FIG. 2 shows a cross-sectional view illustrating relationships of the fields of view of a medical instrument employing a vision system having distal receptors that are toed in toward the center of the instrument.

A vision system for a medical instrument such as a catheter or cannula through which a probe may be introduced may have fairly specific requirements. In particular, wide fields of view may be unnecessary for an instrument that navigates a lumen of limited diameter. Also, a complete and focused viewing may be needed close to the distal end of the instrument. FIG. 2 shows an implementation of the distal end of an instrument 200 using distal receptors 220 that have fields of view 226 that are toed in toward a central axis 210 of tube 110. This may be achieved, for example, by positioning focusing elements 222 closer to central axis 210 than are fiber bundles 224 or by tilting focusing elements 222 toward central axis 210. In an implementation where the distal receptors include image sensor chips, the image sensor chips may similarly be pointed in toward a central axis of the catheter. The toed-in configuration of receptors 220 in FIG. 2 can provide more overlap of the fields of view of receptors 220 near central axis 210 in the object area without needing to expand the individual fields of view of receptors 220. The toed-in configuration may be desirable when the object on which instrument 200 will act is expected to be in front of the distal tip of instrument 200. In an alternative configuration, receptors 220 may be toed-out so that a greater portion of the walls of natural lumen 190 are within the fields of view of receptors 220. A toed-out configuration may be desirable, for example, when instrument 200 is used to examine or act on the walls of natural lumen 190.

Figure 3:
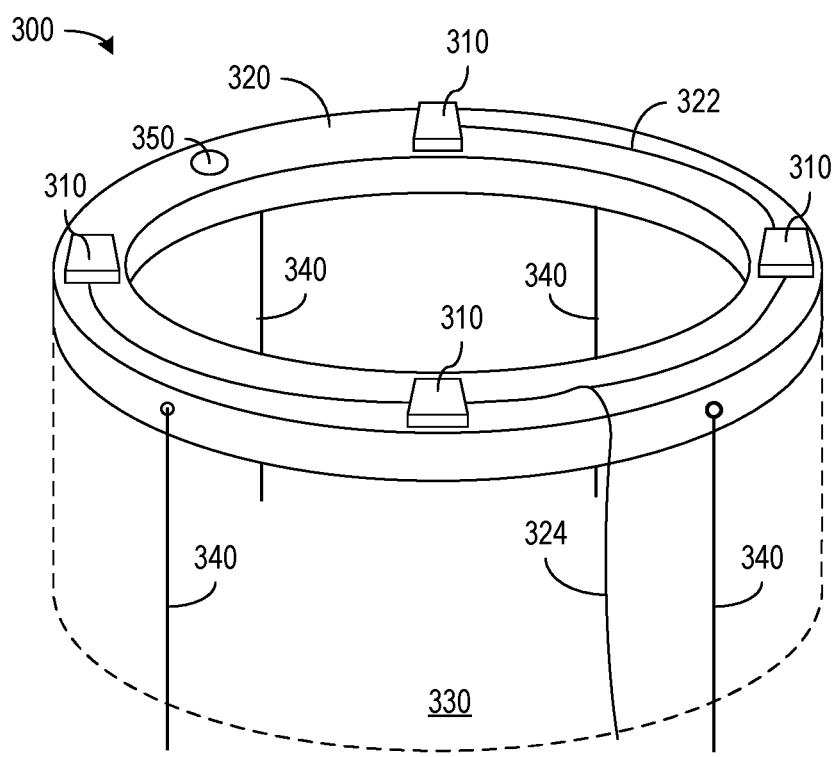
FIG. 3 shows a vision system having image sensor chips mounted on and electrically connected through an annular substrate.

FIG. 3 shows an embodiment of a vision system 300 including distal receptors that are image sensors 310 mounted on an annular substrate 320 at the end of a tube 330. Annular substrate 320 may be sized to fit on the distal end of a medical instrument. For a lung catheter, for example, annular substrate 320 may have a diameter of about 3 mm, a width of about 0.5 mm, and a central opening with a diameter of about 2 mm. Each image sensor 310 may include a CMOS or CCD image sensor chip and an optical system that is sufficiently small for mounting within the width of the annular area of substrate 320. The optical system may be coupled to an image sensor chip to collect light and focus an image on active pixels of the image sensor chip. The light collecting or imaging optics for an image sensing chip is typically about 7 to 10 times as wide as the active sensor area, so an image sensor 310 that is a 0.5 mm wide image may have an active area that is about 0.07×0.07 mm. With current pixel sizes in a range from 0.0012 to 0.0022 mm for current CMOS image sensors, each image sensor 120 may be about 30 to 60 pixels wide.

Figure 4A:
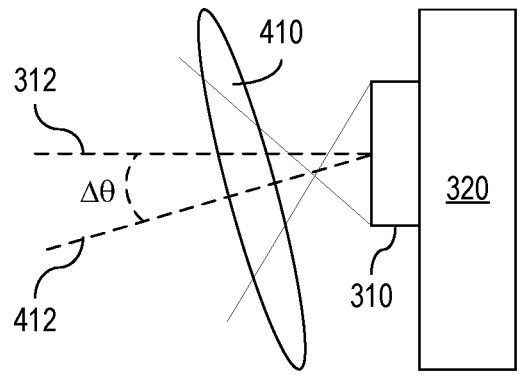
FIGS. 4A, 4B, and 4C illustrated alternative systems for directing the field of view of an image receptor toward a central axis of an annular area.
Figure 4B:
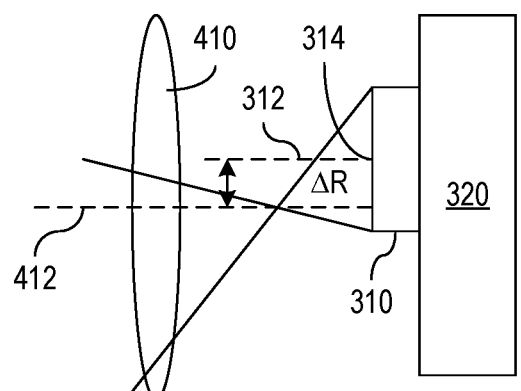

The optical system for each image sensor 310 may provide a field of view that is centered along a direction that is perpendicular to annular substrate 320, toed in toward a central axis of annular substrate 320, or toed out away from the central axis of annular substrate 320. For example, as illustrated in FIG. 4A, a lens 410 that forms an image on the active or imaging area of an image sensor 310 may have an optical axis 412 at a non-zero angle AO with a normal direction 312 of the image sensor 310. Alternatively, as illustrated in FIG. 4B, the optical axis 412 of the lens 410 that forms an image on the active or imaging area of an image sensor 310 may be perpendicular to the active or imaging area of imaging senor 310 but offset from the center 314 of the active area of the imaging sensor 310. In particular, the optical axis 412 of lens 410 may be offset in a direction toward (or away from) a central axis of the annular substrate and by a distance ΔR, so that the sensed object area is biased toward (or away from) the central axis of the annular substrate.

Figure 4C:
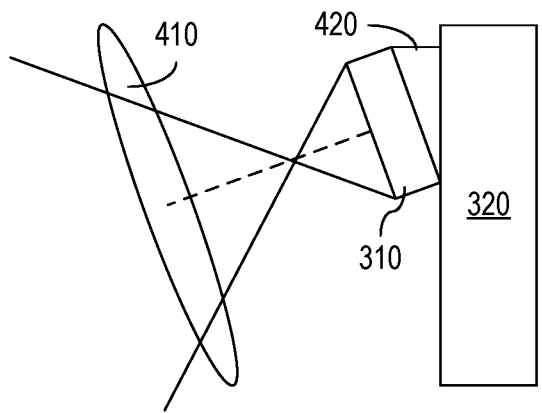

Image sensors 310 may be attached to substrate 320 using imager die attach techniques that are well known for mobile telephones and other devices. Chip scale packaging or attaching lenses of image sensors 310 at the wafer level is also available. As described with reference to FIGS. 4A and 4B, it may be desirable to offset or tilt the lens or optical system of each image sensor 310 relative to the center axis of the active area of the image sensor chip to give the image sensor 310 a field of view that is at an angle to the normal to the chip surface. In which case, image sensors 310 may be mounted flat on substrate 320 and still provide fields of view that are toed in toward or toed out away from a center of annular substrate 320. Alternatively, an optical system with an optical axis centered on and normal to the center of the imaging area of the image sensor 310 can be used, and a wedge 420 as shown in FIG. 4C may be placed under each image sensor 310 if toed-in or toed-out fields of view are desired.

FIG. 3 shows a particular configuration in which four image sensors 310 are used. In general, two, three, or more image sensors 310 could be employed, and the number of image sensors 310 may be selected to provide a desired collective field of view for the type of visual representation, the type of image processing available, and a desired object or in-focus distance range. The arrangement of image sensors 310 may particularly depend on fields of view of image sensors 310, which may, for example, have rectangular cross-sections.

Substrate 320 in alternative embodiments may be a printed circuit board, a ceramic substrate, or other structure capable of electrically connecting image sensors 310. In particular, substrate 320 may include electrically conductive traces 322 that provide power to chips 310 and carry data signals back from chips 310 to an image processing system (not shown). Electrical traces 322 also connect to one or more lead wires 324 that extend from substrate 320 at the distal end of tube 330 back to devices at the proximal end of tube 330. Traces 322 may in particular be connected to reduce the number of lead lines 324 that are required for image sensors 310, which may be an issue when many image sensors 310 are employed and tube 330 is small. In addition to image sensors 310, other electrical components (not shown) such as a signal processing unit or a transmitter can be connected to traces 322 and image sensors 310. In addition, vision system 300 may include a light 350 such as an LED on substrate 320 or an opening through substrate 320 for an optical fiber that guides light from a proximal light source (not shown) to the distal end of tube 330. Alternatively, illumination for annular vision system 300 may be provided in a separate annular region or structure (not shown) that fits within or around substrate 320.

Substrate 320, in addition to providing electrical connections, may provide a mechanical function of the instrument employing vision system 300. For example, substrate 320 may be made sufficiently rigid and durable for attachment of pull wires or actuating tendons 340. Pulling on or applying tension in actuating tendons 340 will then apply forces to substrate 320 and may then cause a flexible distal end of tube 330 to bend in a direction that depends on the forces applied to actuating tendons 340. Accordingly, substrate 320 can be a mechanical component of a steerable section of the instrument.

Figure 5:
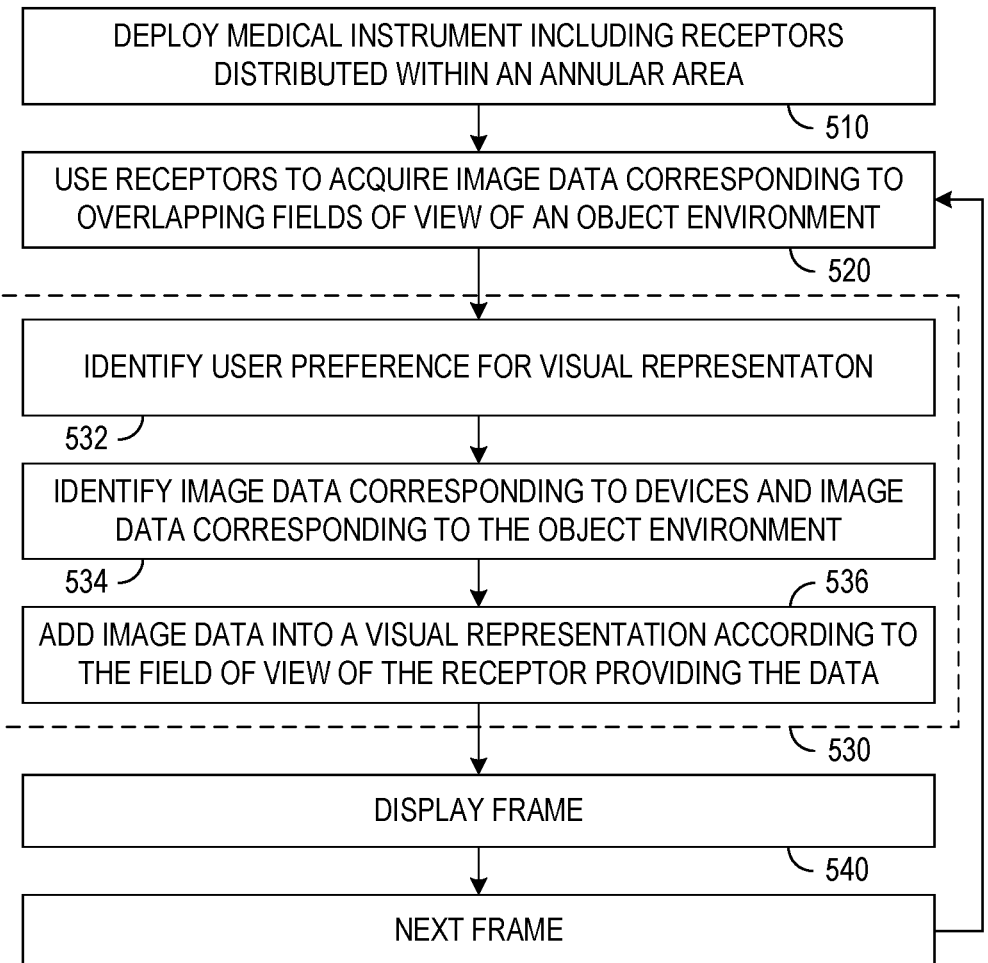
FIG. 5 is a flow diagram of a process for operating a vision system including receptors arranged in an annular area.

FIG. 5 is a flow diagram for a process 500 of using an annular vision system such as described above. For process 500, a step 510 is deployment of an instrument having image receptors distributed in an annular area at the distal tip of the instrument. The instrument may, for example, include a catheter, an endoscope, a cannula, or another guiding instrument that is deployed by having a distal tip of the instrument inserted into a natural lumen such as an airway or bronchial tube. The deployment may further include using the vision system on the distal tip of the instrument to assist in navigating the instrument further along the natural lumen.

The image receptors in step 520 acquire image data, e.g., by directing light that is collected at the distal end of the instrument through optical fibers to an image sensor that produces digitized image data indicating, for example, the brightness and/or color of the light collected. Alternatively, image data can be digitized by image sensors at the distal end of the instrument and transmitted electronically to an image processing system.

Process 500 processes the image data and produces a visual representation of the image data in a step 530. The specific image processing employed can vary widely and depend on the desired type of visual representation and the desired content of the visual representation among other factors. A visual representation may, for example, include a series of frames where each frame corresponds to one or more images or each frame corresponds to a stereoscopic view. The desired content of the visual representation may include or omit specific objects or be visualization from a particular view point or camera angle.

Image processing step 530 of FIG. 5 includes a step 532 of identifying user preferences for the visual representation. For example, a user may have options to select 2D or 3D visual representations, select among available view points, select a number of camera angles simultaneously displayed, and select how image data corresponding to distal portions of the instrument or a probe associated with the instrument will be treated. Alternatively, a vision system may need to provide an image or image data that is sufficient for a human user or an automated system to determine which way a lumen leads or bends, so that a path of navigation can be selected or recorded.

Image processing 530 of FIG. 5 also includes a step 534 of analyzing image data from the receptors to identify image data that represents portions of devices, e.g., of the instrument that includes the vision system or another medical instrument introduced into the object environment during use of the instrument. For example, if the instrument including the vision system is a catheter or other guiding instrument, a probe or other guided instrument that is introduced to the object environment using the guiding instrument may be represented in the image data from one or more distal receptors. Identifying step 534 can use feature recognition techniques or available information on the locations of the receptors and the position and orientation of the instrument and any guided instrument to identify specific image data or pixels representing light reflected from the instrument and any guided instrument. The instrument and any guided instrument may have a specific color or colors that simplify the identification task.

Step 536 combines the image data from some or all of the receptors to construct a frame of the visual representation. Step 536 may use known image stitching techniques that rely on overlap between the image data of the separate receptors. The image stitching process may be simplified in that the relative positions and orientations of the receptors may be fixed and known. Knowledge of the locations and orientations of the receptors may also permit step 536 to generate filler or interpolated values for pixels corresponding to any gaps in the coverage of the fields of view of the receptors. The knowledge of the location and orientation of the receptors may also permit construction of a quantitative 3D model of at least a portion of the object environment and any devices in the object environment. A 3D model may be useful for computerized or robotic manipulations of the instrument. The image stitching process also may use classifications of the image data or pixels found in recognition step 534. For example, specific image data may be classified as representing devices or representing the object environment. The stitching process may include the image data representing the devices to provide a view that a human eye might see, omit image data representing the devices to provide an unobstructed view of the object environment, or combine the image data representing the devices to provide a view in which the devices are semitransparent or shown in outline. In general, omitting the devices or showing the devices as semitransparent or as outlines may require that at least one of the receptors have a clear view of portions of the object environment that are blocked by devices in other views of the receptors. Larger numbers of receptors or greater overlap of the fields of view of the receptors may be desirable for this type of image processing.

The frame of a visual representation can then in step 540 be displayed to a user, e.g., using a monitor or a stereoscopic viewer, while process 500 branches from step 550 back to step 520 to acquire image data and process another frame. Process 500 can thus provide moving images as a stream of frames of a visual representation.

Figure 6:
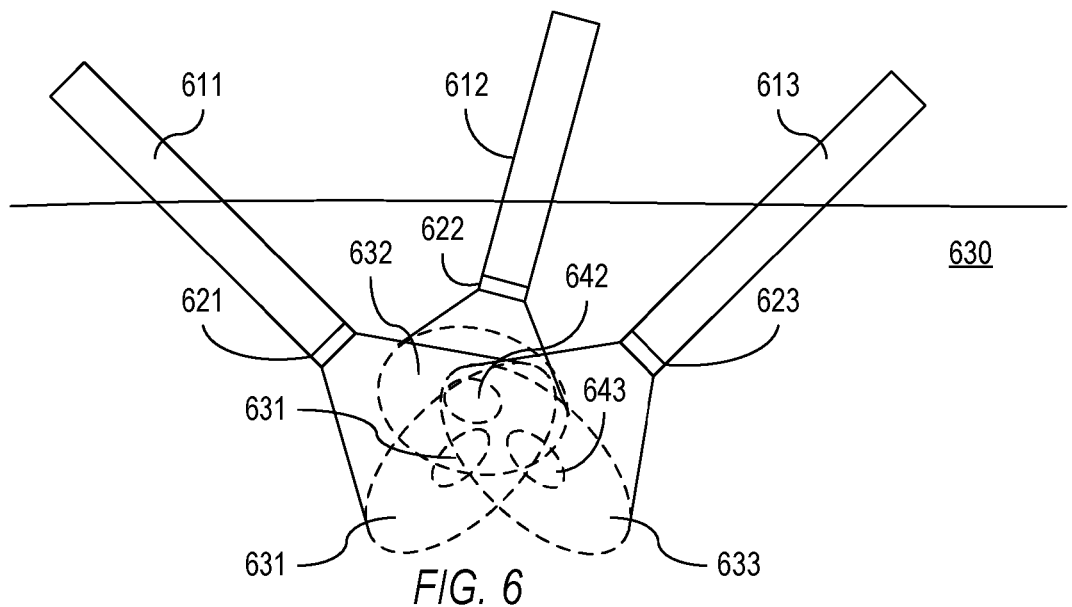
FIG. 6 illustrates a system in accordance with an embodiment of the invention employing multiple annular vision systems.

A single annular vision system, by itself, can generate a visual representation of a desired portion of a surgical environment. However, multiple annular visions systems could also be used co-operatively to form a visual representation. For example, in endoscopic surgery, multiple cannulas 611, 612, and 613 can be inserted or otherwise introduced to a surgical site 630 in a patient as shown in FIG. 6. Each cannula 611, 612, or 613 may include a vision system 621, 622, or 623 that includes an annular region containing distal image receptors as described above. Visual systems 621, 622, and 623 may further include illumination fixtures, for example, in the annular region containing the distal receptors or a separate annular region adjacent to the distal receptors. Annular vision systems 621, 622, and 623 leave the distal openings of cannulas 611, 612, and 613 unobstructed so that medical instruments (not shown) can be insert through cannulas 611, 612, and 613 to perform a medical procedure at site 630. Cannulas 611, 612, and 613 provide vision, so that a separate vision system in an inserted instrument or a separate vision probe in the instrument channel of cannula 611, 612, or 613 or an additional cannula (not shown) is unnecessary. In contrast, some surgical systems may employ one more additional instruments or cannulas specifically for vision systems. The use of annular vision systems 621, 622, and 623 that are part of cannulas 611, 612, and 613 may thus reduce the number of instruments that might otherwise need to be introduced to surgical site 630.

Vision systems 621, 622, and 623 have respective fields of view 631, 632, and 633 that may be annular fields of view. For example, as shown in FIG. 6, fields of view 631, 632, and 633 have respective blind spots 631, 632, and 633, which may result from the optical characteristics, e.g., locations, apertures, and focal lengths, of the distal receptors in vision systems 621, 622, and 623 or may result from the medical instruments (not shown) that extend from the instrument channels of cannulas 611, 612, and 613 and block view of respective central areas 641, 642, and 643. However, the fields of view 631, 632, and 633 of the instrument cannulas 611, 612, and 613 may overlap so that the field of view of one vision system 621, 622, or 623 provides visual information for blind spots 641, 642, or 643 of other vision systems 622, 623, or 621. Position sensors on cannulas 611, 612, and 613 or the instrument manipulators can be used to determine both the relative location and relative orientation of the cannulas 611, 612, and 613 and thus of fields of view 631, 632, and 633 with respect to each other. With the relative orientation and position of the three video frames known, any portion of the images in the combined field of view covered by at least two cameras may be processed in a computer to remove radial and other distortions associated with vision systems 621, 622, and 623 and to merge the images together to form two more natural rectilinear views of at least a portion of surgical site or environment 630 for stereoscopic display to a surgeon. This processing can be performed on raw data directly from the receptors in vision systems 621, 622, and 623 or on image data resulting from processing of data from the receptors to first produce visual representations associated with respective vision systems 621, 622, and 623. Some regions of environment 630 may be covered by more than two cameras, so that identifiable portions of the field of view, such as the instrument shafts, and can be erased or altered in the generated visual representation. Topological information about the surgical site, e.g., acquired from pre-operative data such as Magnetic Resonance Imagers, Ultrasound, or other equipment combined with appropriate computer processing of the image data may used to generate a three-dimensional model of surgical site 630 from which a synthetic perspective view of surgical site 630 can be generated. In other words, processing the raw video information may synthesize two rectilinear views of the surgical site from perspectives other that of the actual camera data. The surgeon or other operator of the system could change this synthetic view to artificially move about surgical site 630, simulating the use of a standard stereo endoscopic camera on a separate probe.

Although the invention has been described with reference to particular embodiments, the description is only an example of the invention's application and should not be taken as a limitation. For example, although a lung catheter was discussed above, the invention applies to medical instruments deployable in body organs such as: brain, nose, throat, lungs, ears, heart, stomach, liver, kidneys, genitals, bladder, peripheral vasculature, to name a few. Various adaptations and combinations of features of the embodiments disclosed are within the scope of the invention as defined by the following claims.

What is claimed is:

1. A method comprising:
   inserting an instrument through a lumen in an elongated guide structure so that an end of the instrument extends from an opening at a distal end of the lumen into a work site;
   capturing image data using a plurality of receptors, each of the receptors comprising an optical system with an optical axis passing through an annular area surrounding the opening at the distal end of the lumen;
   identifying a user preference for a visual representation of the work site; and
   processing the image data to construct the visual representation of the work site, the processing comprising constructing the visual representation to comply with the user preference.

2. The method of claim 1, wherein capturing the image data comprises each of the receptors capturing an image from a field of view covering only a portion of the work site, each of the fields of view overlapping with at least one of the fields of view of the other receptors.

3. The method of claim 2, wherein processing the image data further comprises stitching together overlapping images respectively from the receptors to construct the visual representation of the work site.

4. The method of claim 1, wherein the visual representation comprises a stereoscopic view of the work site.

5. The method of claim 1, wherein processing the image data further comprises removing the instrument from the visual representation to permit viewing of portions of the work site that the instrument would otherwise block from being viewed in the visual representation.

6. The method of claim 1, wherein processing the image data further comprises making the instrument semitransparent in the visual representation to permit viewing of the work site through the instrument.

7. The method of claim 1, wherein processing the image data further comprises showing the instrument as an outline in the visual representation to permit viewing of the work site through the instrument.

8. The method of claim 1, wherein each of the receptors comprises a lens at a distal end of a bundle containing a plurality of optical fibers.

9. The method of claim 1, wherein each of the receptors comprises an image sensor chip located adjacent to the annular area.

10. The method of claim 9, wherein in each of the receptors, the optical system has an optical axis that is offset from a center of an active region of the image sensor chip.

11. The method of claim 1, wherein the plurality of receptors comprises at least three receptors.

12. The method of claim 1, wherein the optical axes are at respective non-zero angles with a central axis of the annular area.

13. The method of claim 1, wherein the user preference comprises one or more of:
an option to select 2D or 3D for the visual representation;
an option to select among available view points for the visual representation;
an option to select a number of camera angles simultaneously displayed in the visual representation; and
an option to select how the instrument is represented in the visual representation.

14. A method comprising:
inserting an instrument through a lumen in an elongated guide structure so that an end of the instrument extends from an opening at a distal end of the lumen into a work site;
capturing image data using a plurality of receptors, each of the receptors comprising an optical system with an optical axis passing through an annular area surrounding the opening at the distal end of the lumen;
identifying image data corresponding to light reflected from the instrument; and
applying a user preference to determine whether or how the image data identified to represent the instrument is employed in a visual representation.

15. The method of claim 14, wherein the user preference selects one of:
the instrument being shown in the visual representation;
the instrument being removed from the visual representation;
the instrument being semitransparent in the visual representation; and
an outline of the instrument being shown in the visual representation.

16. The method of claim 14, wherein capturing the image data comprises each of the receptors capturing an image from a field of view covering only a portion of the work site, each of the fields of view overlapping with at least one of the fields of view of the other receptors.

17. The method of claim 16, further comprising stitching together overlapping images respectively from the receptors to construct the visual representation of the work site.

18. The method of claim 14, wherein the visual representation comprises a stereoscopic view of the work site.

19. The method of claim 14, further comprising removing the instrument from the visual representation to permit viewing of portions of the work site that the instrument would otherwise block from being viewed in the visual representation.

20. The method of claim 14, further comprises making the instrument semitransparent in the visual representation to permit viewing of the work site through the instrument.

* * * * *